US00PP09075P

United States Patent [19]

VandenBerg

[11] Patent Number: Plant 9,075

[45] Date of Patent: Mar. 14, 1995

[54] CHRYSANTHEMUM PLANT NAMED HARVEST EMILY

[75] Inventor: Cornelis P. VandenBerg, Salinas, Calif.

[73] Assignee: Yoder Brothers, Inc., Barberton, Ohio

[21] Appl. No.: 151,973

[22] Filed: Nov. 15, 1993

[51] Int. Cl.[6] ..... A01H 5/00

[52] U.S. Cl. ..... Plt./79

[58] Field of Search ..... Plt. 76, 79, 74.1, 82.3

[56] References Cited

U.S. PATENT DOCUMENTS 4,616,099 10/1986 Sparkes ..... 47/58

OTHER PUBLICATIONS

Broertjes, et al. 1980, "A mutant of a . . . Irradiation of progressive radiation-induced mutants in a mutation breeding programme with *Chrysanthemum morifolium*", Euphytica, 29:526-530.

Gosling, ed., 1979, "The Chrysanthemum Manual-6th edition", The National Chrysanthemum Society, London, Essex Telegraph Press, Ltd., pp. 329-336.

Broertjes, et al., 1978, "Application of Mutation Breeding Methods in the Improvement of Vegetatively Propapated Crops", Elsevier Sci. Pub. Co., New York, pp. 162-175.

Searle, et al., 1968, "Chrysanthemum The Year Round", Blanford Press, London, pp. 27-29, 320-327.

Chan, 1966, "Chysanthemum and rose mutations induced by X-rays", Am. Soc. Hort. Sci. Proc., pp. 613-620.

Broertjes, 1966, "Mutation breeding of chrysanthemums", Euphytica, 15:156-162.

Dowrick, et al., 1966, "The induction of mutations in chrysanthemum using X- and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Harvest Emily particularly characterized by its flat capitulum form; decorative capitulum type with many disc florets, especially in spring flowerings; vivid orange ray floret color, with darker orange-bronze center of the flower; diameter across face of capitulum of 57 to 70 mm when fully opened; branching pattern is spreading and prolific, with 8 to 9 breaks after pinch when grown outside under natural daylength in fall flowerings, and 6 to 7 breaks after pinch when grown in 10 cm pots for spring flowerings; natural season flower date of August 13 to 19 when planting rooted cuttings on June 21 to 23 in Salinas, Calif., and of September 15 when planting rooted cuttings June 11 in Hightstown, N.J.; flowering response of 45 to 48 days after rooting in no light/no shade programs in spring; plant height of 38 cm when grown in fall under natural daylength with no growth regulators in New Jersey, of 23 to 25 cm when grown in fall under natural daylength in California, and of 23 to 25 cm when grown in 10 cm pots in spring with 0 to 2 applications of 2500 ppm B-9 SP; and durable, uniform performance.

1 Drawing Sheet

The present invention comprises a new and distinct cultivar of Chrysanthemum, botanically known as *Dendranthema grandiflora* and referred to by the cultivar name Harvest Emily.

Harvest Emily, identified as 8486 (87-284D01), is a product of a mutation induction program. The new cultivar was discovered and selected by Cornelis P. VandenBerg on Jun. 22, 1990, in a controlled environment in Salinas, Calif. as one flowering plant within a flowering block established as rooted cuttings from stock plants which had been exposed as unrooted cuttings to an X-ray source of 2000 rads in Fort Myers, Fla. on Nov. 30, 1989. The irradiated parent cultivar was the cultivar identified as Emily, disclosed in U.S. Plant Pat. No. 7,754, and described as a garden mum with a flat decorative flower with many disc florets; light pink ray floret color, with darker center of the flower; diameter across face of capitulum of 57 to 70 mm when fully opened; spreading and prolific branching pattern, with 8 to 9 breaks after pinch when grown outside under natural daylength in fall flowerings, and 6 to 7 breaks after pinch when grown in 10 cm pots for spring flowerings; natural season flowering date of August 13 to 25 when planting rooted cuttings June 21 to 23 in Salinas, Calif., and September 16 to 29 when planting rooted cuttings June 15 to 18 in Hightstown, N.J.; flowering response of 45 to 48 days after rooting in no light/no shade programs in spring; plant height of 36 to 38 cm when grown in fall under natural daylength with no growth regulators in New Jersey, of 23 to 25 cm when grown in fall under natural daylength with no growth regulators in California, and of 20 to 25 cm when grown in 10 cm pots in spring with 0 to 2 applications of 2500 ppm B-9 SP. The ranges of measurements for Emily given here are somewhat wider than the measurements given in the patent description for Emily. This is based on continuing flowering trials of Emily after filing the plant patent application for Emily.

The irradiation program resulting in Harvest Emily had as its primary objective the expansion of color ranges of the parent cultivar Emily. The irradiation program comprised irradiating cuttings of the parent cultivar at irradiation levels of 1750 and 2000 rads. A total of 1073 cuttings harvested from a total of 150 irradiated plants were planted on Apr. 23 and 16, 1990, respectively. Of these, 17 initial selections were made, which selections were then revegetated and reflowered. Three consecutive flowerings resulted in discarding 12 of the original 17 selections on Mar. 5, 1991. The remaining five selections were maintained as PIs (Possible Introductions) and further trialed in Salinas, Calif., Hightstown, N.J. and Leamington, Ontario, Canada, ultimately resulting in the decision to discard code 8492 on Oct. 1, 1992, to discard code 8484 on Nov. 4, 1992, and to introduce selection 8486 as Harvest Emily, selection 8485 as Blushing Emily and selection 8476 as Cheery Emily. Blushing Emily and Cheery Emily are disclosed in pending application Ser. Nos. 08/151,975 and 08/151,974, respectively.

The first act of asexual reproduction of Harvest Emily was accomplished when vegetative cuttings were taken from the initial selection in August 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Harvest Emily are firmly fixed and are retained through successive generations of asexual reproduction.

Harvest Emily has not been observed under all possible environmental conditions. The phenotype may vary significantly with variations in environment such as temperature, light intensity and daylength, without, however, any variation in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characterisitcs of Harvest Emily, which, in combination, distinguish this Chrysanthemum as a new and distinct cultivar:

1. Flat capitulum form.
2. Decorative capitulum type with many disc florets, especially in spring flowerings.
3. Vivid orange ray floret color, with darker orange-bronze center of the flower.
4. Diameter across face of capitulum of 57 to 70 mm when fully opened.
5. Branching pattern is spreading and prolific, with 8 to 9 breaks after pinch when grown outside under natural daylength in fall flowerings, and 6 to 7 breaks after pinch when grown in 10 cm pots for spring flowerings.
6. Natural season flower date of August 13 to 19 when planting rooted cuttings on June 21 to June 23 in Salinas, Calif., and of September 15 when planting rooted cuttings June 11 in Hightstown, N.J.
7. Flowering response of 45 to 48 days after rooting in no light/no shade programs in spring.
8. Plant height of 38 cm when grown in fall under natural daylength with no growth regulators in New Jersey, 23 to 25 cm when grown in fall under natural daylength in California, and 23 to 25 cm when grown in 10 cm pots in spring with 0 to 2 applications of 2500 ppm B-9 SP.
9. Durable, uniform performance.

The accompanying photographic drawing is a color photograph of Harvest Emily grown as a pinched garden mum under natural season outside conditions in Salinas, Calif., with the colors being as nearly true as possible with illustrations of this type. Plants were grown outside and dug and transplanted into 15 cm bulb pans at flowering time for photography purposes.

Of the commercial cultivars known to the inventor, the most similar in comparison to Harvest Emily is the parent cultivar Emily. In the above description of Harvest Emily the ranges of values for Harvest Emily are much narrower than the ranges of values given for Emily. This is based on the fact that Emily was flowered over many years, while Harvest Emily was flowered over a period of only one and a half years. All traits of Harvest Emily are similar to those of Emily, except for the ray floret color. The ray floret color of Harvest Emily is vivid orange with a darker orange-bronze center of the flower, while the ray floret color of Emily is light pink wtih a darker center of the flower.

In the following description, color references are made to the Royal Horticultural Society Colour Chart. The color values were determined on plant material grown as a pinched garden mum grown under natural season outside conditions in Salinas, Calif. on Aug. 16, 1993.

Classification

*Botanical.*—*Dendranthema grandiflora* cv Harvest Emily.

*Commercial.*—Flat decorative spray pot mum and garden mum.

INFLORESCENCE

A. Capitulum:

*Form.*—Flat.

*Type.*—Decorative with many disc florets, especially in spring flowerings.

*Diameter across face.*—57 to 70 mm when fully opened.

B. Corolla of ray florets:

*Color (general tonality from a distance of three meters).*—Vivid orange with darker orange-bronze center of the flower.

*Color (upper surface).*—167C, overlaid with 168B. Center of capitulum 169B.

*Color (under surface).*—22A, streaked with 178D.

*Shape.*—Flat, straight, rounded petal tips.

C. Corolla of disc florets:

*Color (mature).*—6B.

*Color (immature).*—2A, overlaid with 144B.

D. Reproductive organs:

*Androecium.*—Present on disc florets only, moderate pollen.

*Gynoecium.*—Present on both ray and disc florets.

PLANT

A. General appearance:

*Height.*—38 cm when grown in fall under natural daylength with no growth regulators in New Jersey, 23 to 25 cm when grown in fall under natural daylength in California, and 23 to 25 cm when grown in 10 cm pots in spring with 0 to 2 applications of 2500 ppm B-9 SP.

*Branching pattern.*—Spreading and prolific, with 8 to 9 breaks after pinch when grown outside under natural daylength in fall flowerings, and 6 to 7 breaks after pinch when grown in 10 cm pots for spring flowerings.

B. Foliage:

*Color (upper surface).*—147A.

*Color (under surface).*—147B.

*Shape.*—Relatively small, shallow lobes, and slightly serrated.

I claim:

1. A new and distinct Chrysanthemum plant named Harvest Emily, as described and illustrated.

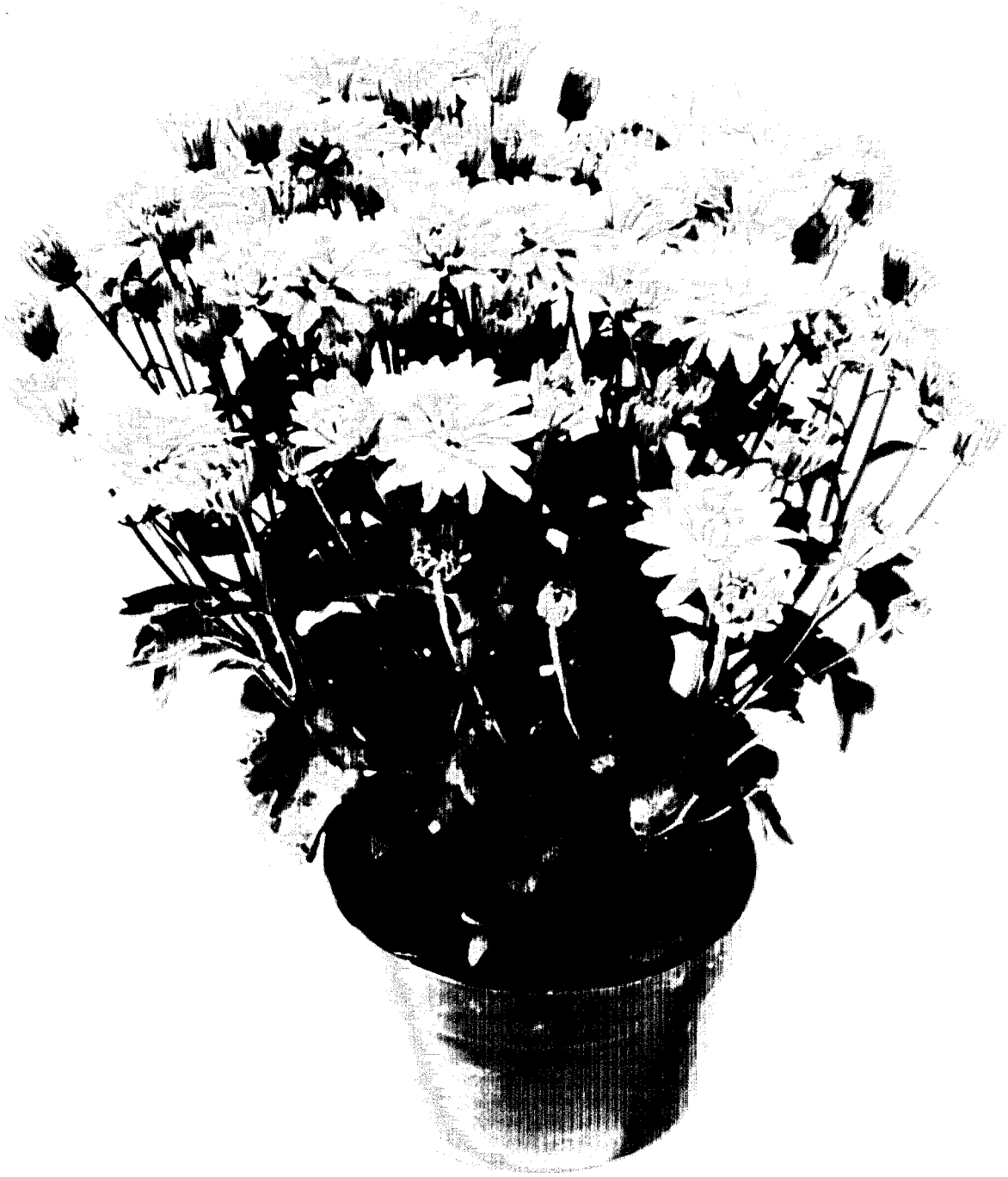

* * * * *